US00PP07829P

United States Patent [19]

Chamberlin, Sr.

[11] Patent Number: Plant 7,829

[45] Date of Patent: Mar. 17, 1992

[54] 'RED SUN' PEACH TREE

[75] Inventor: Thomas O. Chamberlin, Sr., Visalia, Calif.

[73] Assignee: Metropolitan Life Insurance Company, Overland Park, Kans.

[21] Appl. No.: 526,495

[22] Filed: May 21, 1990

[51] Int. Cl.[5] ..... A01H 5/00

[52] U.S. Cl. ..... Plt./43

[58] Field of Search ..... Plt./43, 43.2, 43.3

[56] References Cited

U.S. PATENT DOCUMENTS

Plt. 6,008 9/1987 Chamberlin, Sr. ..... Plt. 43

*Primary Examiner*—Howard J. Locker

*Attorney, Agent, or Firm*—Worrel & Worrel

[57] ABSTRACT

A new and distinct variety of peach tree which produces fruit which is mature for harvesting and shipment approximately August 20 to August 25 in the central San Joaquin Valley of California, the fruit being freestone by nature having a round shape and which further exhibits a full red coloration in shades of light red to dark red and a pleasing, very crisp yellow flesh.

1 Drawing Sheet

BACKGROUND OF THE NEW VARIETY

The present invention relates to a new and distinct variety of peach tree which will hereinafter be denominated varietally as 'Red Sun' and more particularly to a peach tree which produces freestone fruit which is mature for commercial harvesting and shipment approximately August 20 to August 25 in the San Joaquin Valley of central California, and which is further distinguished by clear, very crisp yellow flesh, and a full red skin coloration varying from shades of light red to dark red and which has noteworthy shipping and handling characteristics.

ORIGIN AND ASEXUAL REPRODUCTION OF THE NEW VARIETY

The present variety of peach tree hereof was discovered by the inventor in a nursery located in Del Rey, Calif. The inventor discovered the new variety of peach tree as a chance seedling in the nursery. The seed of the new variety was contained in a mixed lot of seed of unknown parentage which was collected in the fall of 1978 and planted in the nursery in the early spring of 1979. The first fruit produced by these chance seedlings was first observed in 1981. The fruit produced by the new variety of the present invention denominated 'Red Sun' was found to be freestone and to have characteristics of skin color, shape, flesh color, texture and harvest date which were thought to warrant further testing.

As stated, the 'Red Sun' peach tree is of unknown parentage. The mixed lot of seed producing the different varieties of seedlings from which it was selected came from a row of miscellaneous unknown varieties of peach and nectarine trees. The inventor is not aware of a commercial variety of peach tree to which the 'Red Sun' peach tree of the present invention could be compared for any useful purpose. Perhaps the closest varieties of which the inventor is aware are the 'Ryan's Sun' peach tree (U.S. Plant Pat. No. 5,103) and the 'September Sun' peach tree (U.S. Plant Pat. No. 6,008). This similarity is largely only as to ripening date in that the 'Red Sun' peach tree ripens approximately six to eight days after the 'Ryan's Sun' peach tree and about ten to twelve days before the 'September Sun' peach tree.

Buds were collected from the seedlings of the 'Red Sun' peach tree in 1981 and 1982. Trees were budded to the new variety in a test block in the nursery in early spring of 1982. The first fruit of the asexually reproduced trees of the new variety was observed in 1983 and the fruit has been observed each year since then. The trees of the new variety, including the fruit thereof, have consistently retained the same characteristics which are described and claimed herein and which caused the new variety to be selected for further development in the first place.

SUMMARY OF THE NEW VARIETY

The 'Red Sun' peach tree is characterized as to novelty by producing a freestone fruit which has a full red coloration including shades of light red to dark red at harvest. The flesh is clear yellow with a bright red pit cavity. The size of the fruit is generally from 6.985 cm (2¾ inches) to 8.255 cm (3¼ inches) in diameter with a full round shape and a medium wide base. The fruit has a good flavor and the flesh has a very crisp texture at harvest time which is approximately August 20 to August 25 in the San Joaquin Valley of central California.

BRIEF DESCRIPTION OF THE DRAWING

The accompanying drawing is a photograph showing fruit of the new variety including one in side elevation, a second sectioned and laid open to show one half with the stone cavity exposed and the other half with the stone in place, a third in top plan view to reveal the stem cavity, a fourth in bottom plan view showing the apex end portion, and a fifth in side elevation showing the suture thereof; and representative foliage of the new variety.

DETAILED DESCRIPTION

Referring more specifically to the pomological details of this new and distinct variety of peach tree, the following has been observed under the ecological conditions prevailing at the nursery of origin which is located in Del Rey, Calif. All major color code designations are by reference to the Inter-Society Color Council-National Bureau of Standards color name charts.

TREE

Generally:
- *Size.*—Normal with upright growth.
- *Figure.*—Normal.
- *Productivity.*—Very good.
- *Regularity of bearing.*—Will bear very well every year.

Trunk:
- *Size.*—Diameter in relation to length — Normal.
- *Surface texture.*—Normal rough peach bark.
- *Color.*—Grey brown (62 d gy br).
- *Lenticels.*—Numbers — About 8 to 10 per square inch. Color — (53 m.o.).

Branches:
- *Size.*—Normal.
- *Surface texture.*—Normal. Same as trunk.
- *Color.*—Grey brown (62 d gy br).
- *Lenticels.*—Numbers — About 8 to 10 per square inch. Color — (53 m.o.).

LEAVES

Size:
- *Generally.*—Normal.
- *Average length.*—12.7 cm (5 inches) to 13.97 cm (5½ inches).
- *Average width.*—3.33375 cm (1-5/16 inches) to 4.445 cm (1¾ inches).

Form:
- *Shape.*—Lanceolate.

Color:
- *Upwardly disposed surface.*—Dark green (127 gy 01 g).
- *Downwardly disposed surface.*—Lighter green (125 m 01 g).

Marginal form: Serrate.

Glandular characteristics: Reniform, one pair at base of leaf.

Base of leaf: Acute.

Apex of leaf: Acumate.

Petiole:
- *Length.*—About 1.11125 cm (7/16 inch).
- *Width.*—About 0.15875 cm (1/16 inch).

Stem glands:
- *Form.*—Reniform.
- *Position.*—Generally one pair found at base of leaf.
- *Pattern.*—Found in pairs opposite each other.
- *Size.*—Small, about 0.079375 cm (1/32 inch).

FLOWERS

Flower buds:
- *Size.*—At the start of red bud stage — Length — 0.9525 cm (⅜ inch); Diameter — 0.79375 cm (5/16 inch).
- *Shape.*—Slightly elongate.
- *Color.*—Petals mostly (22 grey) with some (19 gy red) at base petals.

Flowers:
- *Generally.*—Large showy pink blossoms.
- *Date of bloom.*—End of February to March 1 at Del Rey, Calif. all of the tree achieves full bloom in approximately eight days.
- *Size.*—Generally — Length — 1.905 cm (¾ inch); Diameter — 1.74625 cm (11/16 inch).
- *Shape.*—Very slightly elongated.
- *Petals.*—Light pink about ¾ of outer part of petal (252 p p pink); base of petal (249 l p pink).

FRUIT

Maturity when described: Ripe for commercial harvesting and shipment approximately August 20 to August 25 at Del Rey, Calif.

Size:
- *Generally.*—Uniformity — Very good, very round with wide base with rounded to almost flat apex area.
- *Average diameter.*—About 6.985 cm (2¾ inches) to 8.255 cm (3¼ inches).
- *Average diameter transverse in the suture plane-*.—7.9375 cm (3⅛ inches).
- *Average diameter transverse and at right angles to the suture plane.*—About 6.985 cm (2¾ inches) to 8.255 cm (3¼ inches).

Form:
- *Uniformity.*—Very good.
- *Symmetry.*—Symmetrical.

Suture:
- *Generally.*—Smooth.
- *Length.*—From base to apex about 9.8425 cm (2⅞ inches).

Ventral surface: Rounded to slightly flat.

Stem cavity: Rounded about 0.9525 cm (⅜ inch) deep.

Base: Wide and slightly rounded.

Apex: Rounded to slightly flat.

Pistil point: Small, almost receded.

Stem:
- *Length.*—0.9525 cm (⅜ inch).
- *Diameter.*—0.3175 (⅛ inch).

Skin:
- *Thickness.*—Medium.
- *Texture.*—Smooth and tenacious to flesh.
- *Tendency to crack.*—None.
- *Pubescence.*—Medium.
- *Color.*—Dark red (16 d. Red) to light red (27 deep y. pink). The skin coloration of the new variety has a faint yellow ground color and excellent uniformity.
- *Flesh color.*—Yellow (83 brill y). There is approximately a five to ten percent (5 to 10%) red flecking characteristically present in the flesh extending outwardly from the pit cavity depending upon the ripeness of the fruit.
- *Surface of pit cavity.*—Rough.
- *Color of pit cavity.*—Dark red (13 deep red).

Juice production: Medium juicy and very mild.

Flavor: Mild, good.

Aroma: Slight.

Fibers: Not fibrous.

Ripening: Even.

Eating quality: Crisp with mild flavor at harvest.

Stone:
- *Attachment.*—Freestone.
- *Fibers.*—None.
- *Size.*—Length — 3.4925 cm (1⅜ inches).
- Width— 2.69875 cm (1-1/16 inches).
- Thickness— 2.06375 cm (13/16 inch).
- *Form.*—Ovid.
- *Apex.*—Pointed.
- *Color.*—Dry — Dark brown (58 m br).
- *Base.*—Small and flat.
- *Sides.*—Rough.
- *Ridges.*—Medium deep about 0.15875 cm (1/16 inch deep).
- *Tendency to split.*—None.

Use: Fresh market.

Keeping quality: Very good, has been kept in storage for over three weeks.

Shipping and handling qualities: Due to crisp nature and skin tenacion to flesh, will handle and ship very well.

Although the new variety of peach tree possesses the described characteristics noted above as a result of the growing conditions prevailing near Del Rey in the Central part of the San Joaquin Valley of Central California, it is to be understood that variations of the usual magnitude and characteristics incident to changes in growing conditions, fertilization, pruning and pest control are to be expected.

Having thus described and illustrated my new variety of peach tree, what I claim as new and desire to be secured by Plant Letters Patent is:

1. A new and distinct variety of peach tree substantially as illustrated and described and which produces freestone fruit which is mature for harvesting and shipment approximately August 20 to August 25 in the San Joaquin Valley of central California, the fruit having a full red skin coloration varying in shades from light red to dark red, a bright red pit cavity and with red flecking characteristically present extending outwardly from the pit cavity into flesh which is clear yellow and of a very crisp texture with skin tenacious to the flesh thereby having excellent shipping and handling characteristics.

* * * * *

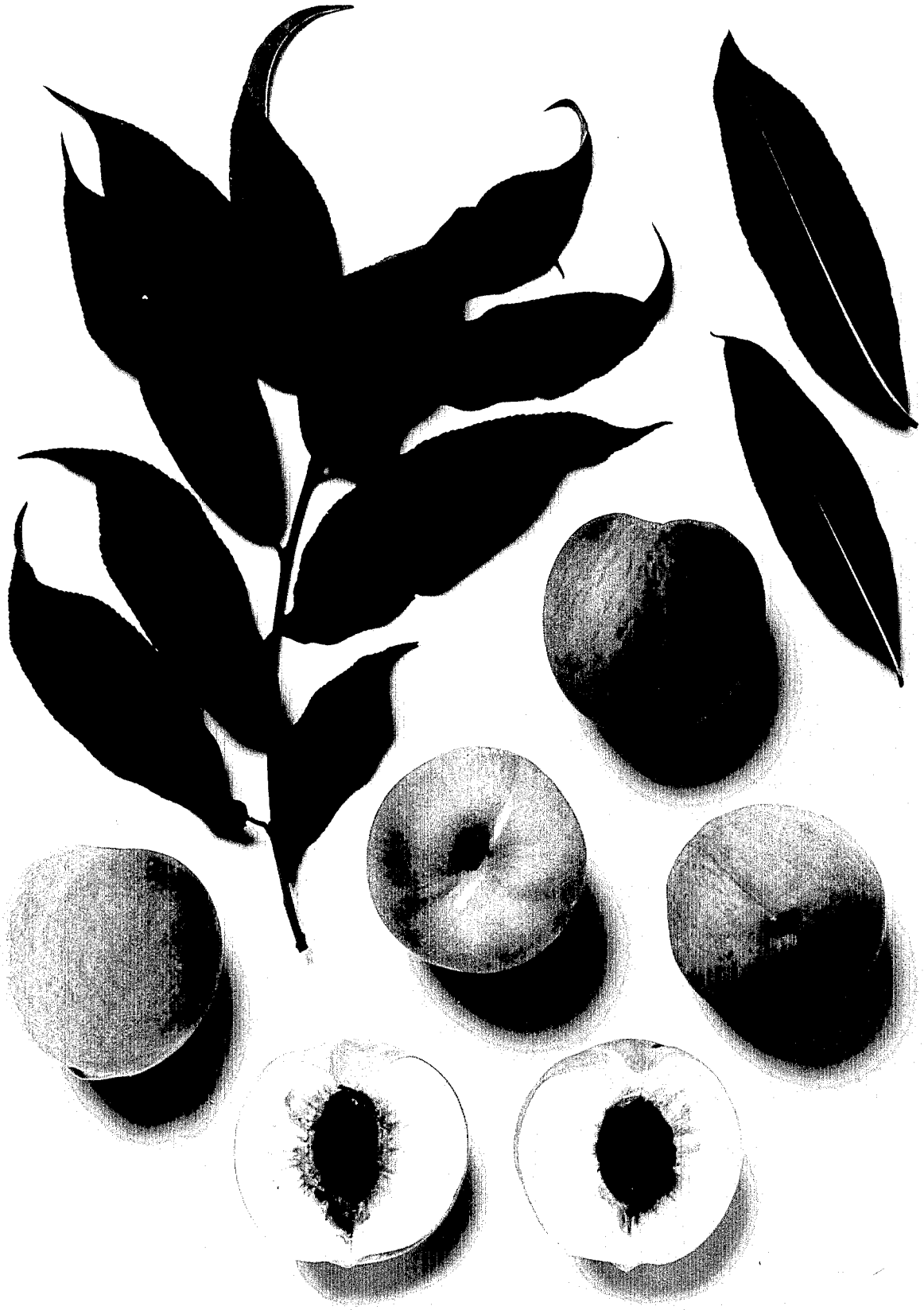

UNITED STATES PATENT AND TRADEMARK OFFICE

CERTIFICATE OF CORRECTION

PATENT NO. : Plant 7,829

DATED : March 17, 1992

INVENTOR(S) : Thomas O. Chamberlin, Sr.

It is certified that error appears in the above-identified patent and that said Letters Patent is hereby corrected as shown below:

Column 3, Line 58, between "base" and "petals", insert --of--

Column 4, Line 22, delete "2 7/8" and substitute --3 7/8--

Column 4, Line 30, delete "5/8" and substitute --3/8--

Signed and Sealed this

First Day of June, 1993

*Attest:*

Michael K. Kirk

MICHAEL K. KIRK

*Attesting Officer*

*Acting Commissioner of Patents and Trademarks*